US008643371B2

(12) United States Patent
Yang et al.

(10) Patent No.: US 8,643,371 B2
(45) Date of Patent: Feb. 4, 2014

(54) LOW MAGNETIC FIELD RESONANCE SYSTEM

(75) Inventors: Shieh-Yueh Yang, New Taipei County (TW); Hong-Chang Yang, New Taipei County (TW); Herng-Er Horng, New Taipei County (TW); Shu-Hsien Liao, New Taipei County (TW)

(73) Assignee: Magqu Co. Ltd., New Taipei County (TW)

( * ) Notice: Subject to any disclaimer, the term of this patent is extended or adjusted under 35 U.S.C. 154(b) by 219 days.

(21) Appl. No.: 13/205,851

(22) Filed: Aug. 9, 2011

(65) Prior Publication Data

US 2012/0032680 A1    Feb. 9, 2012

(30) Foreign Application Priority Data

Aug. 9, 2010    (TW) .............................. 99126532 A

(51) Int. Cl.
*G01V 3/00*    (2006.01)

(52) U.S. Cl.
USPC .......................................... 324/321; 324/322

(58) Field of Classification Search
USPC .................. 324/321, 322, 318, 307, 306, 300
See application file for complete search history.

(56) References Cited

U.S. PATENT DOCUMENTS

| 4,899,111 A * | 2/1990 | Pines et al. .................... 324/321 |
| 4,968,938 A * | 11/1990 | Pines et al. .................... 324/321 |
| 4,968,939 A * | 11/1990 | Pines et al. .................... 324/321 |
| 7,498,812 B2 * | 3/2009 | Doty ............................ 324/318 |
| 8,106,657 B2 * | 1/2012 | Sakellariou et al. .......... 324/321 |
| 2011/0115486 A1 | 5/2011 | Frohlich et al. |

* cited by examiner

*Primary Examiner* — Louis Arana
(74) *Attorney, Agent, or Firm* — WPAT, P.C.; Anthony King

(57) ABSTRACT

The invention provides a low-field nuclear magnetic resonance system for measuring a magnetic resonance signal of an object. The low-field nuclear magnetic resonance system includes a pre-magnetization module, a uniform magnetic field coil module, a pulse and receiving coil module, a filter amplifier module, a signal acquisition module and a processing module. The pre-magnetization module is used to establish a pre-magnetization field in the object to increase magnetization of the object. The uniform magnetic field coil module is used to change a resonance frequency and background magnetic field intensity of the object during nuclear magnetic resonance measurement by regulating a magnetic field of the coil. The processing module further includes a programming object for controlling timing processing and signal analysis of the measurement process.

10 Claims, 14 Drawing Sheets

LOW MAGNETIC FIELD RESONANCE SYSTEM

BACKGROUND OF THE INVENTION

1. Field of the Invention

The invention relates to a low-field nuclear magnetic resonance system, in particular to a low-field nuclear magnetic resonance system for pre-magnetizing an object to be measured and capable of adjusting a resonance frequency and background magnetic field intensity during regulation nuclear magnetic resonance measurement.

2. Description of Related Art

From the viewpoint of quantum mechanics for the existing nuclear magnetic resonance (NMR) technique, as the proton number and the mass number are of an odd number, the magnetic quantum number (I) of a nucleus is not zero. For example, for hydrogen, I=½. In such a situation, if the nucleus is placed in an externally applied magnetic field, the spin magnetic torque will be split into two energy levels, i.e. a low energy level of forward magnetic field (upward spin magnetic torque) and a high energy level of reverse magnetic field (downward spin magnetic torque). The energy difference $\Delta E = h \gamma B_0$, in which h is a reduced Planck Constant, and $\gamma$ is a gyromagnetic ratio, for example, $\gamma$ of $^1H$ being equal to 42.58 MHz/Tesla. According to Boltzmann Distribution Law, the distributed population of the magnetic torque in the low energy is higher than that in the high energy and the ratio of $N\downarrow/N\uparrow$ is:

$$\frac{N\downarrow}{N\uparrow} = \exp\left(-\frac{\Delta E}{kT}\right),$$

wherein, $\Delta E$ is the energy difference between the upward spin magnetic torque and the downward spin magnetic torque, k is Boltzmann's Constant, $1.3805 \times 10^{-23}$ J/Kelvin, and T is the temperature of a spin system (Kelvin's temperature standard).

Much of the distributed population is in the state of upward spin magnetic torque, resulting in net magnetization being in the z direction (as $B_0$ is the z direction). At this time, if a pulse ($B_1$) of the same precession frequency (Larmor frequency) of the nucleus is applied in the y direction, such that the nucleus obtains energy, the net magnetization will be deviated to the x axis and the angle of deviation is correlated with the time of pulse on and the strength thereof. As the angle of deviation of the net magnetization is 90°, it is called a 90° pulse. As the angle of deviation of the net magnetization is 180°, it is called a 180° pulse. The relation between the angle of deviation and the time t of the externally applied pulse is $\theta = \gamma B_1 t$. At pulse off, the net magnetization is effected by $B_0$, rendering the magnetization of deviation to make precession along the direction of magnetization (z axis). Due to the precession of the magnetization incorporating with relaxation of the magnetization to be recovered to a balance state (z axis), the magnetization forms a track of a top. As the nucleus returns to a base state from the stimulated state, there are mainly two independent components surrounding the externally applied magnetic field for precession, i.e. spin-lattice relation, being a recovery of the z component with its relaxation time constant called longitudinal relation time $T_1$, and spin-spin relaxation, in which the x-y component returns to zero with its relaxation time constant called transverse relaxation time $T_2$. The relation of the net magnetization is:

$$M_{x'y'}(t) = M_{x'y'}(O_+) \exp(-t/T_2)$$

$$M_z(t) = M_{z,o}[1 - \exp(-t/T_1)] + M_z(O_+) \exp(-t/T_2)$$

The track of the magnetization will direct an oscillation current to be recorded. Such situation is just like a projection on two mutually vertical planes of the top-like track. It is called a free induced declining (FID) signal. After Fourier Transformation of the FID signal, a spectrum signal of the NMR is obtained, as shown in FIG. 1.

Low-field NMR is a branch of the NMR and is regarding earth's field NMR or NMR in an extremely low, human-made magnetic field and being shielded (or compensated) by the earth field. Differing from the magnitude of the magnetic field traditionally used in NMR being in 1.5 T~4 T, the low-field NMR makes use the magnitude of the magnetic field being in the grade of µT or nT, while making use of super conducting quantum interference devices as sensors. Meanwhile, the low-field NMR provides the following advantages: (1) narrow bandwidth of the magnetic resonance; (2) magnetizing artifact resulting from high magnetic field being tremendously reduced; and (3) no need of super conductive coil, i.e. reducing cost. However, the NMR still has a defect, i.e. the signal of the low-field NMR being far smaller than that of the traditional NMR system.

SUMMARY OF THE INVENTION

As such, the present invention on one hand provides a low-field nuclear magnetic resonance system for measuring a magnetic resonance signal of an object to be measured, comprising:

a pre-magnetization module including at least two magnets having the same size, the pre-magnetization module forming a receiving space between the two magnets to receive the object to be measured and establishing a pre-magnetization field for the object to be measured;

a uniform magnetic field coil module including a tilt angle adjusting unit and a magnetic field coil unit, in which the tilt angle adjusting unit comprises a tilt bottom base, being adjustable in its tilt angle, and the magnetic field coil unit is placed on an inclined plane of the tilt bottom base and comprises a coil set and a power source, wherein the coil set includes two pairs of coils with different radius, being allocated in a concentric circle manner and being electrically connected to the power source, thereby adjusting background magnetic field intensity of the magnetic resonance;

a pulse and receiving coil module including a pulse coil a receiving coil and a preamplifier, in which the pulse coil provides a pulse magnetic field for changing a direction of an atomic nuclear magnetic torque of the object to be measured, the receiving coil detects a precession magnetic signal of the magnetic torque and outputs an electric signal to be fed to the preamplifier, and the preamplifier outputs a first amplified signal;

a filter amplifier module including a filter amplifier circuit, for receiving the first amplified signal, filtering noise and outputting a second amplified signal;

a signal acquisition module being respectively electrically connected with the pulse coil and the filter amplifier module for receiving the second amplified signal and outputting an acquisition signal; and a processing module electrically connected to the signal acquisition module, for receiving and analyzing to process the acquisition signal.

In the invention, the pre-magnetization module is used to increase magnetization of the object to be measured.

The uniform magnetic field coil module is capable of adjusting the direction of the magnetic field of the coil set to be in the same direction as the earth's field via adjusting the tilt angle and horizontal direction of the tilt angle adjusting unit. At this time, the background magnetic field intensity of the magnetic resonance in the invention is the earth's field plus the magnetic field supplied by the coil set (B=Bearth+Bcoil). Therefore, the resonance frequency and background magnetic field intensity of the object to be measured during magnetic resonance measurement can be altered by regulating the magnetic field strength of the coil.

The preamplifier of the pulse and receiving coil module in the invention receives an electrical signal and outputs a first amplified signal to reduce the extent of being affected by environment noise when transmitting a weak signal.

In the filter amplifier module of the invention, the filter amplifier circuit is used for filtering noise and outputting a second amplified signal so as to filter the noise outside the resonance frequency to raise signal-noise ratio.

In a preferred embodiment of the invention, the magnet is an Nd—Fe—B magnet.

In a preferred embodiment of the invention, the magnitude of the angle adjustable for the tilt angle is 0-50 degrees.

In a preferred embodiment of the invention, the power source is a DC source.

In a preferred embodiment of the invention, the pulse and receiving coil module is placed in an Aluminum shielding box.

In a particular preferred embodiment of the invention, the receiving coil and the preamplifier of the pulse and receiving coil module are respectively placed in an Aluminum shielding box further, thereby reducing influence by environment AC noise.

The invention, on the other hand, provides a low-field nuclear magnetic resonance system as described above, in which the processing module further includes a programming object for controlling time processing and signal analysis during the measurement process.

In a preferred embodiment, the programming object provides a function of nuclear magnetic resonance measurement, $T_2^*$ fitting measurement or gyromagnetic ratio analysis, or a combination thereof.

Still further, the low-field nuclear magnetic resonance system of the invention provides a use in the object to be measured for measuring a nuclear magnetic resonance result, spin-spin relaxation parameter or gyromagnetic ratio data, or a combination thereof.

Still further, the low-field nuclear magnetic resonance system of the invention provides a use in the object to be measured for measuring a J-coupling detection.

The embodiments of the invention will be explained in detail hereinafter. It will be clearer when referring to description of implementation, features, concepts and advantages of the invention, while viewing the accompanied drawings.

DETAILED DESCRIPTION OF THE PREFERRED EMBODIMENT

In the preferred embodiments, most particular detailed part is explained to have an overall understanding of the invention. However, those skilled in the art should know that without such description of the particular detail, the invention can still be implemented. In other embodiments, the known method, step and material are not described in detail to avoid ambiguity of the invention.

Figure 1:
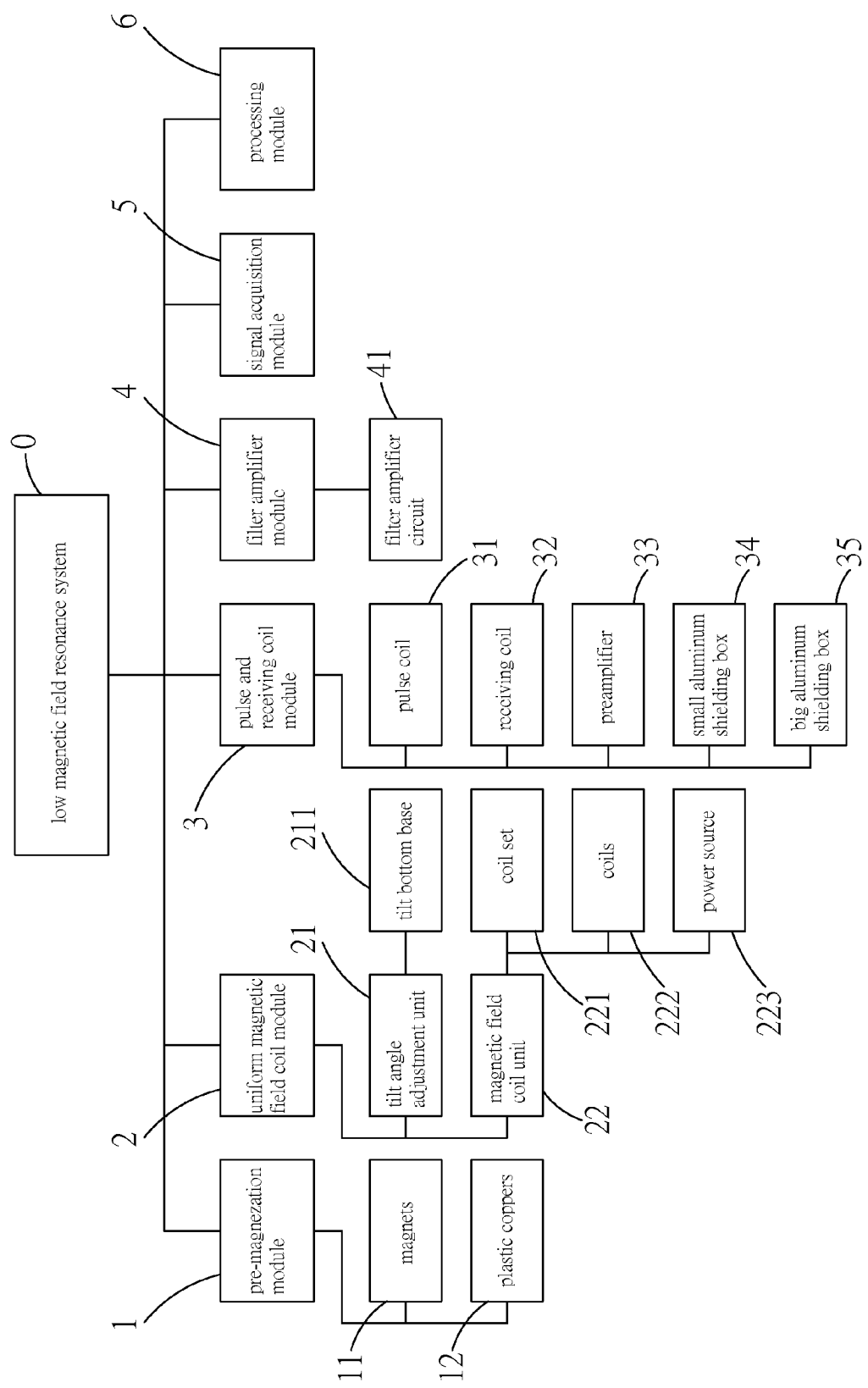
FIG. 1 shows a structural system diagram according to a preferred embodiment of the invention.
Figure 2:
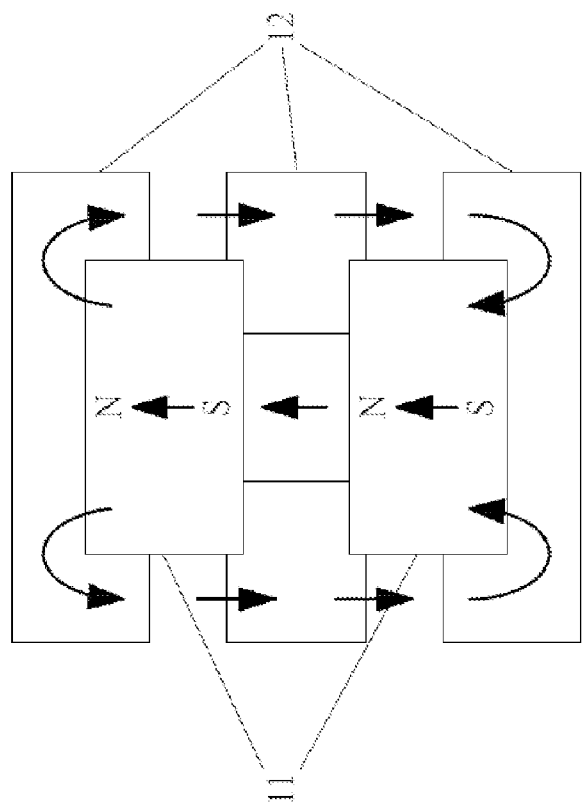
FIG. 2 shows a schematic diagram of a pre-magnetization module of the system according to the preferred embodiment of the invention.
Figure 8:
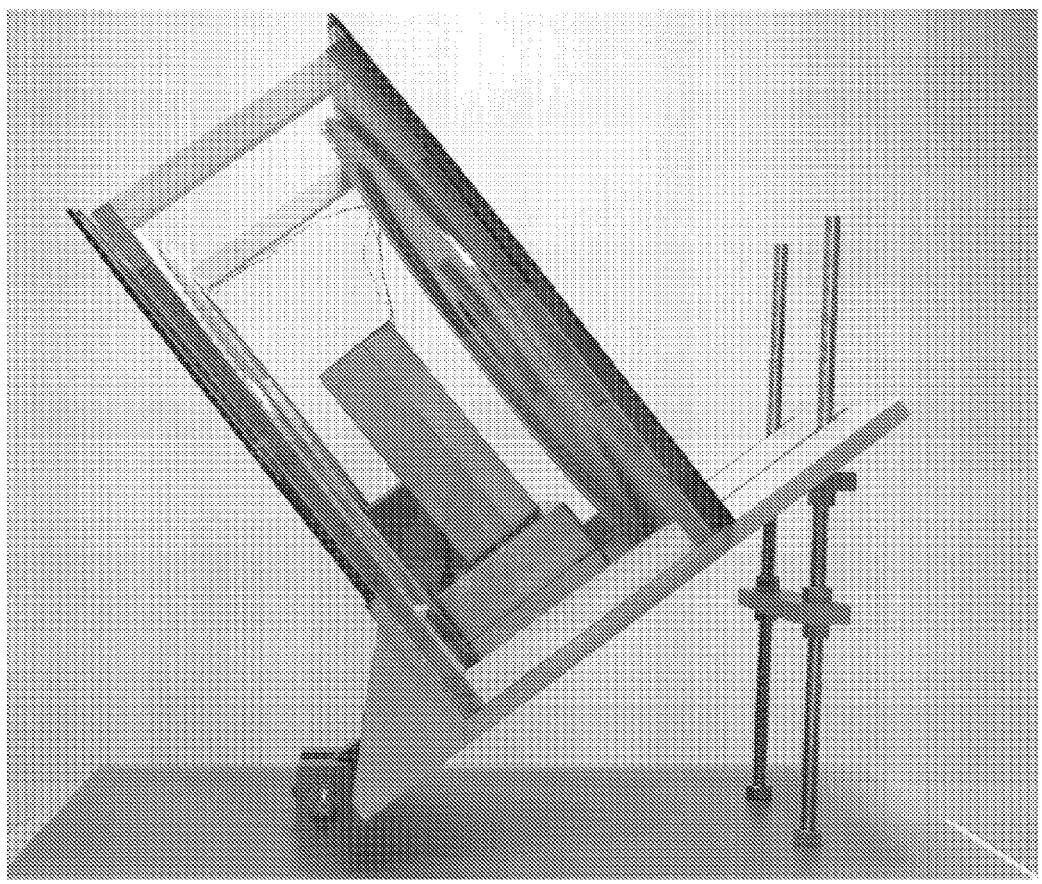
FIG. 8 shows an external appearance diagram according to the preferred embodiment of the invention.

Please refer to FIG. 1, showing a structural system diagram according to a preferred embodiment of the invention, and to FIG. 8, showing an external appearance diagram according to the preferred embodiment of the invention. The preferred embodiment of the invention is a low-field nuclear magnetic resonance system 0 for measuring a magnetic resonance signal of an object to be measured, comprising: a pre-magnetization module 1, including two magnets 11 having the same size and being installed in plastic formed coppers 12, a receiving space being formed between the two magnets 11 to receive the object to be measured and establishing a pre-magnetization field to increase magnetization for the object to be measured. The magnets 11 in the embodiment are of Nd—Fe—B magnet in a size of 5 cm×5 cm×5 cm with an intermediate magnetic field intensity capable of reaching 0.7 Tesla. The structure thereof is shown in FIG. 2.

Figure 3:
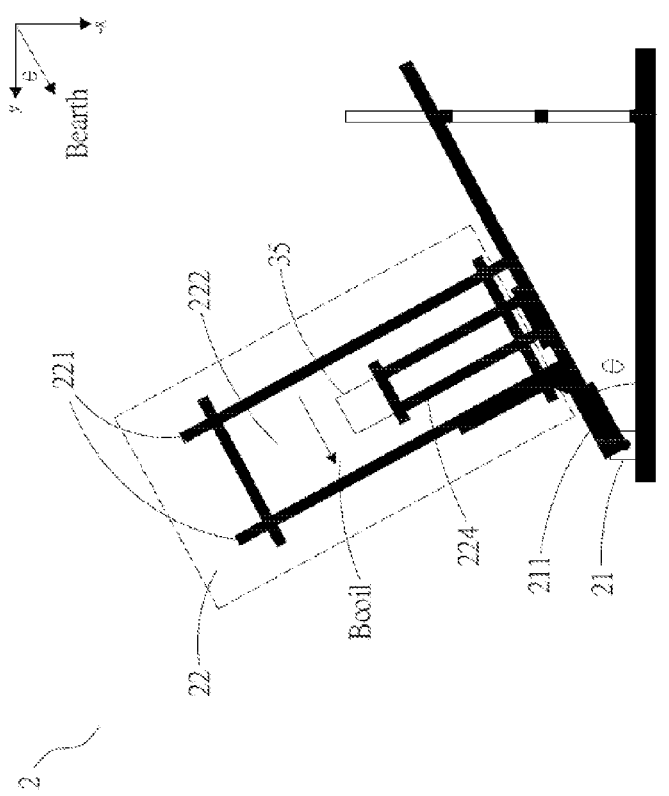
FIG. 3 shows a schematic allocation diagram of a uniform magnetic field coil module and a pulse and receiving coil module of the system according to the preferred embodiment of the invention (in which Bcoil is in a direction of the magnetic field of the coil and Bearth is in a direction of the earth's field)

As shown in FIG. 3, the system further comprises a uniform magnetic field coil module 2, including a tilt angle adjusting unit 21 and a magnetic field coil unit 22. The tilt angle adjusting unit 21 comprises a tilt bottom base 211, being adjustable in its tile angle, and the magnitude of the angle adjustable for the tilt angle is 0-50 degrees. The magnetic field coil unit 22 comprises a coil set 221. The coil set 221 includes two pairs of coils 222 with a different radius and is electrically connected to a power source 223. The magnetic field coil unit 22 is placed on an inclined plane of the tilt bottom base 211 and includes a sample tray 224 for receiving therein an object to be measured. The direction of the magnetic field of the coil set 221 may be adjusted in the same direction as the earth field via adjusting the tilt angle and horizontal direction of the tilt angle adjusting unit 21. At this time, the background magnetic field intensity of the magnetic resonance in the invention is the earth's field intensity plus the magnetic field supplied by the coil set 221 (B=Bearth+Bcoil). Therefore, the resonance frequency and background magnetic field intensity of the object to be measured during magnetic resonance measurement can be altered by regulating the magnetic field of the coil 222. In this embodiment, the radiuses respectively of the two pairs of coils 222 are 24.3 cm and 8 cm, which are placed in a concentric circular manner. In addition, the distance between coils of the same pair 222 is 20 cm. It may be known via data simulation that as the coil turns of the coils 222 having a radius of 24.3 cm are 70 turns and those of the coil having a radius of 8 cm are 2 turns, an optimum uniformity can be obtained. The non-uniformity of the magnetic field is 5/10,000 at a cubic of 4 cm×4 cm×4 cm in the center. The magnetic field intensity provided by the coils 222 is 2.945 gauss/A. The power source makes use of TWIN-TEX TP-1303XT and is a DC power source, in which the current may reach upward to 1 ampere with precision of 1 milli-ampere.

Figure 4:
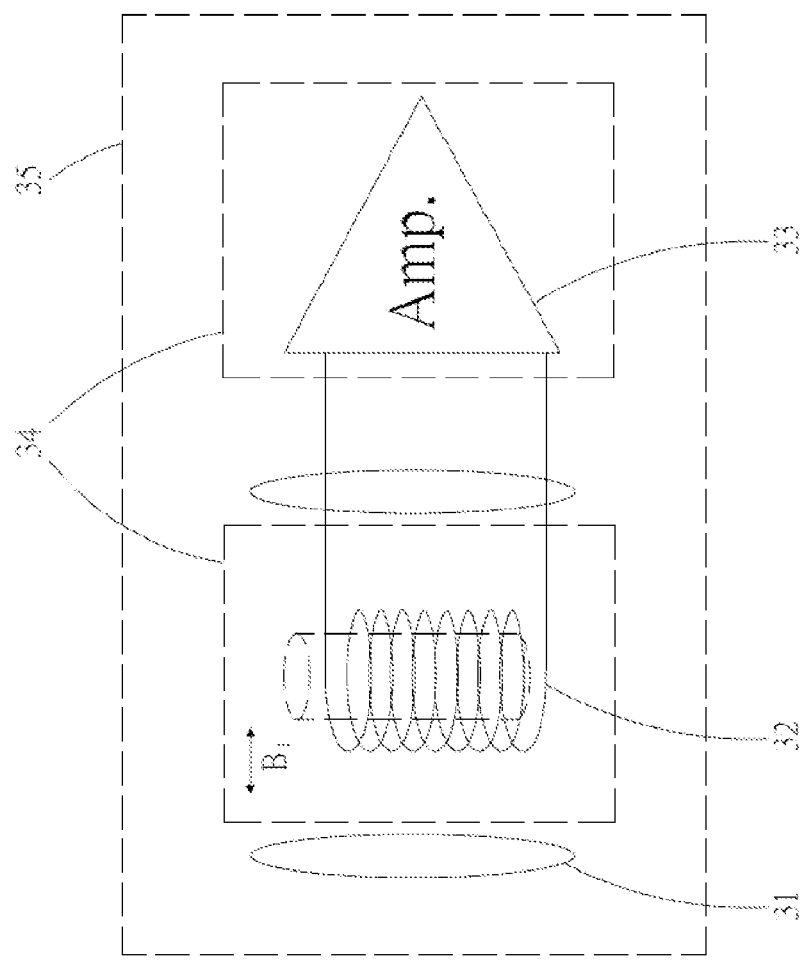
FIG. 4 shows a schematic diagram of the pulse and receiving coil module of the system according to the preferred embodiment of the invention.

Please refer to FIG. 3 together with FIG. 4. The system further comprises a pulse and receiving coil module 3, including a pulse coil 31, a receiving coil 32 and a preamplifier 33, in which the pulse coil 31 provides a pulse magnetic field for changing a direction of an atomic nuclear magnetic torque of the object to be measured, the receiving coil 32 detects a precession magnetic signal of the magnetic torque and outputs an electric signal to be fed to the preamplifier 33, and the preamplifier 33 outputs a first amplified signal after receiving so as to reduce the extent of being affected by environment noise when transmitting a weak signal. Further, the receiving coil 32 and the preamplifier 33 of the pulse and receiving coil module 3 are respectively placed in a small Aluminum shielding box 34 and then placed in a big Aluminum shielding box 35 altogether so as to reduce the influence by environment AC noise.

The system further comprises a filter amplifier module 4, including a filter amplifier circuit 41 to receive the first amplified signal, and to filter noise and output a second amplified signal so as to filter out the noise outside the resonance frequency to raise signal-noise ratio. The filter amplifier module 4 adopted in the embodiment includes a Butherworth high pass filter in a 5 grade and a Butherworth low pass filter in a 2 grade with the cut-off frequency respectively of 1.3 KHz and 10 KHz. In addition, the amplification rate of the circuit is 40 times.

The system further comprises a signal acquisition module 5, being respectively electrically connected with the pulse coil 31 and the filter amplifier module 4 for receiving the second amplified signal and outputting an acquisition signal. In this embodiment, the signal acquisition module 5 is NI USB-6211, in which a terminal AO0 is wired via a BNC terminal for supplying pulse magnetic field power to the pulse coil 31, and via the preamplifier 33 and filter amplifier circuit 41, the magnetic resonance signal received from the receiving coil 32 is transferred to an AI0 terminal from wiring of the BNC terminal and then transferred via the USB terminal.

The system further comprises a processing module 6, being a computer in this embodiment and electrically connected to the signal acquisition module 5 for receiving and analyzing to process the acquisition signal via the USB terminal.

Figure 5:
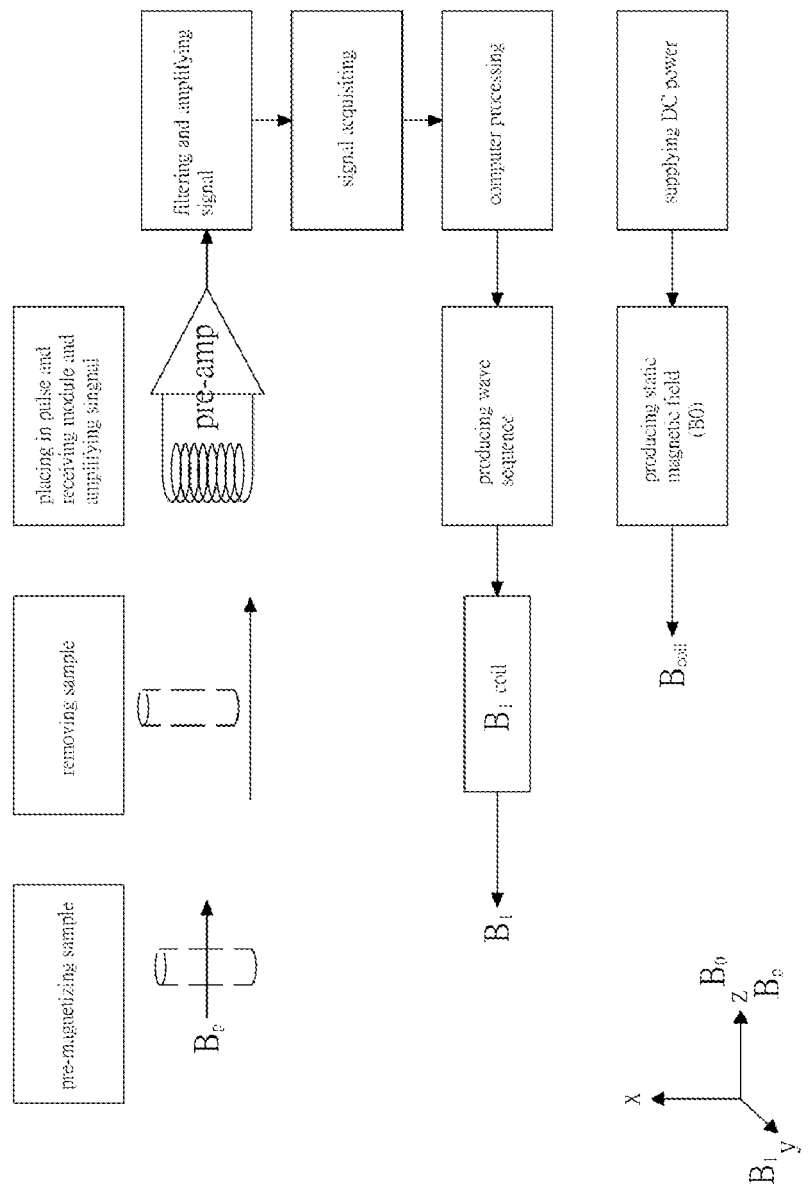
FIG. 5 shows a block diagram in flow of system operation according to the preferred embodiment of the invention (in which $B_p$: pre-magnetized field; $B_0$: static magnetic field; $B_1$: magnetic field of the pulse and Bcoil: magnetic field of the coil)
Figure 6:
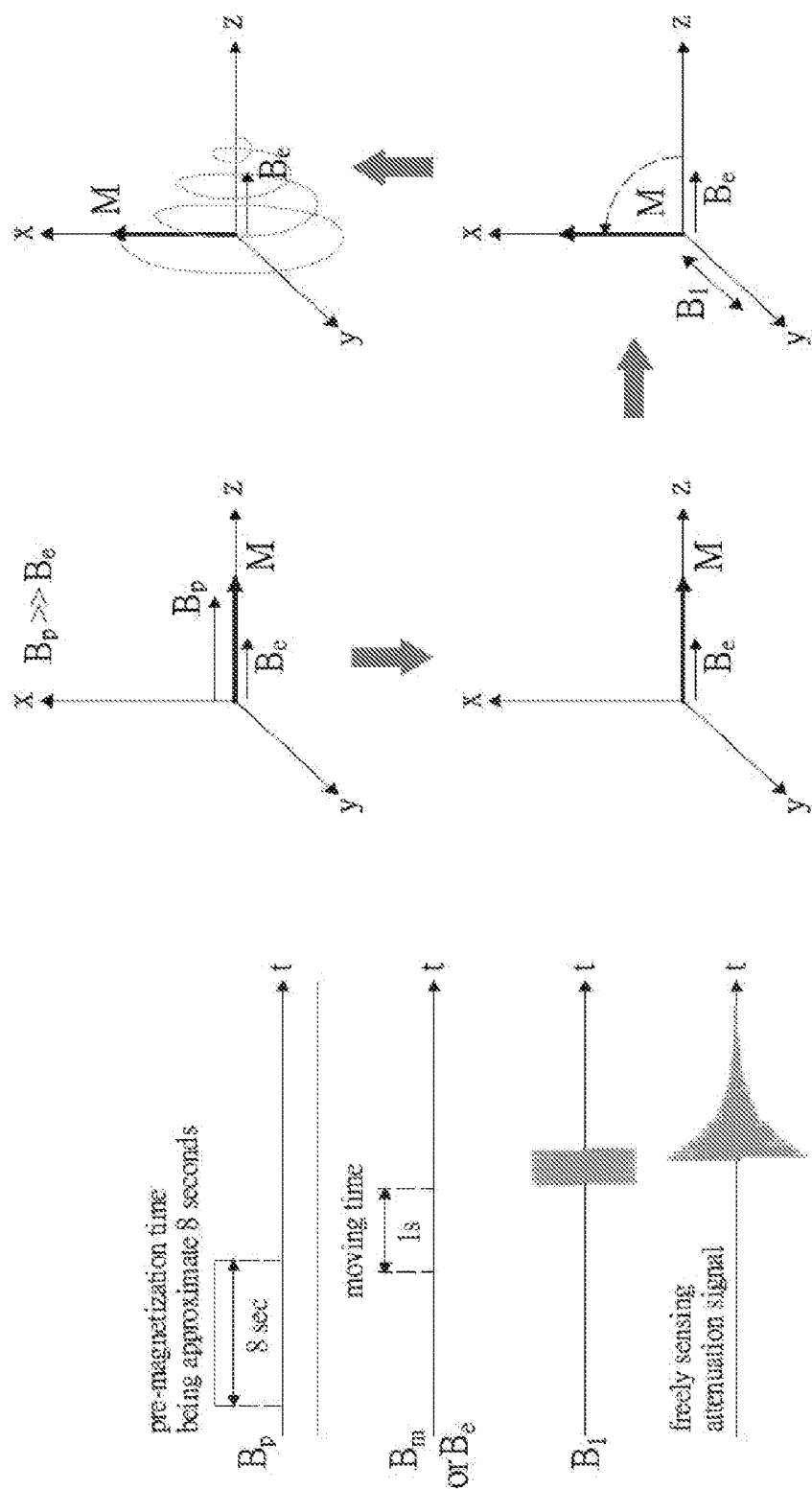
FIG. 6 shows a schematic diagram in magnetized dynamics of an object to be measured of the invention and a waveform sequencing diagram thereof.

During experimenting, the object to be measured is first placed in the pre-magnetization module 1 to increase the magnetized quantity of the object to be measured, while adjusting the resonance frequency and the background magnetic field intensity by the uniform magnetic field coil module 2. Then the object to be measured is moved inside the pulse and receiving coil module 3 for applying a $B_1$ pulse and the receiving magnetic resonance signal. A signal produced thereby is amplified by the filter amplifier module 4, acquired by the signal acquisition module 5 and transferred to the processing module 6. The flow block diagram is shown in FIG. 5. The waveform sequencing diagram and magnetic dynamics are shown in FIG. 6.

After obtaining the magnetic resonance signal, it may analyze $T_2^*$ relaxation time of the object to be measured and calculate the gyromagnetic ratio of the object to be measured via changing the background magnetic field intensity to measure a magnetic resonance frequency by the uniform magnetic field coil module 2.

Figure 9:
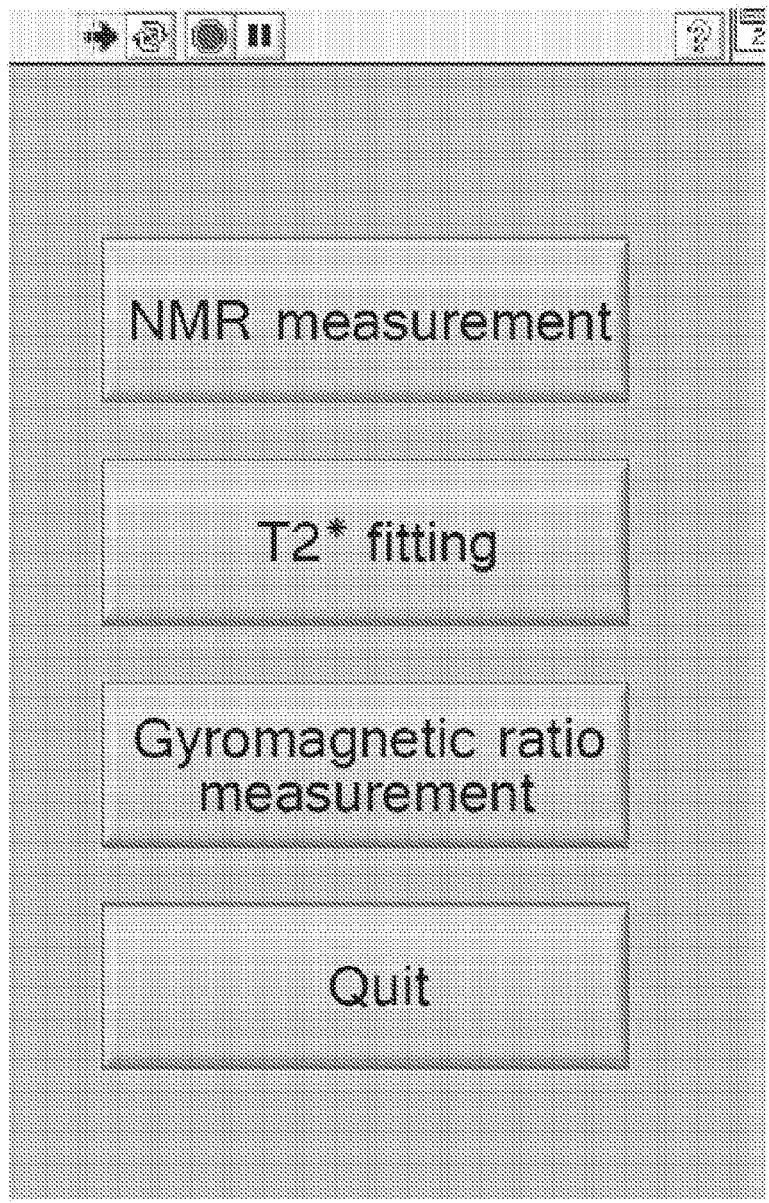
FIG. 9 shows a master window of an operational software of an NMR system according to the preferred embodiment of the invention.

In this embodiment, the system further comprises a system operational software of magnetic resonance to deal with and control timing process and signal analyzing in an experimental procedure of magnetic resonance, to control the NI-USB 6211 to provide a pulse magnetic field during the control time and receiving a reading signal, and to provide the function of software filter, Fourier Transformation, $T_2^*$ fitting and analysis of the gyromagnetic ratio. In the software part as shown in FIG. 9, function areas are divided into three blocks: NMR measurement, $T_2^*$ fitting and gyromagnetic ratio measurement, in which NMR measurement to provide a user simply to proceed with the NMR measurement and Fourier Transformation, $T_2^*$ fitting is to proceed with the $T_2^*$ fitting measurement with respect to data after being measured by the NMR measurement so as to calculate the $T_2^*$ relaxation time, and the gyromagnetic ratio measurement enables the user to repetitively proceed with magnetic resonance experiments to record down the resonance frequency and the magnetic field provided by $B_0$ coil and then to proceed with the gyromagnetic ratio analysis to obtain earth's field intensity and the gyromagnetic ratio.

The operational flow of the operational software of the magnetic resonance system is detailed as follows:

1. NMR Measurement

Figure 10:
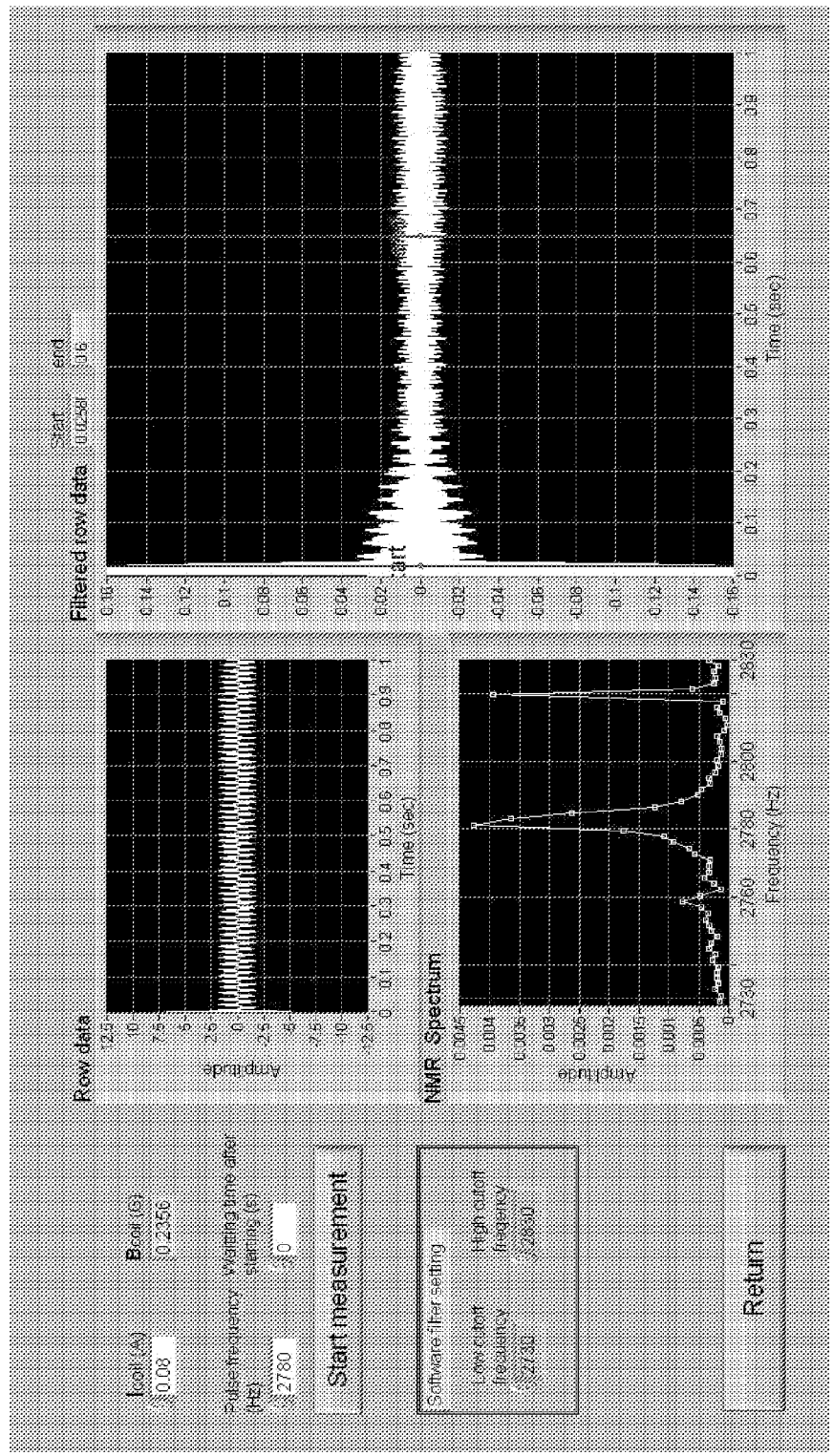
FIG. 10 shows window 1 for NMR measurement of the operational software of the NMR system according to the preferred embodiment of the invention.

After clicking "NMR measure", a new window will appear as shown in FIG. 10.

It will be explained first with respect to setting parameters shown in left-hand side of the drawing.

a. Icoil (A): Please enter the current supplied by the power source, while the magnitude of the magnetic field provided by the coil will be calculated at Bcoil (G).

b. Pulse frequency: It is a pulse frequency output by the pulse coil.

c. Waiting time after starting: After clicking "Start measurement", it may set the time required to start the supply of the pulse for proceeding with the magnetic resonance experiment.

d. Software filter setting: It may set the frequency range of the software filter, in which the preset value is Pulse frequency +−50 Hz and may be automatically adjusted in dependence of the Pulse frequency set in each experiment.

During experimenting, the user should first place the object to be measured, such as water, in the pre-magnetization module statically for 8-10 seconds to pre-magnetize the sample, while setting parameters on the panel, including Icoil, Pulse frequency, and Waiting time after starting=0. After that, the sample is rapidly removed out from the pre-magnetization module and place in the pulse and receiving coil module. Subsequently, it is required to click "Start measurement" on the software window. At this time, the system will give the pulse magnetic field and record down the magnetic resonance signal on the software window and option of the window will be altered as shown in the drawing. Such a portion in experimental operation is the same as NMR measurement and mainly provides the user to alter Icoil and Pulse frequency so as to proceed with magnetic resonance experiments in different magnetic fields and to record the resonance frequency, thereby calculating the gyromagnetic ratio and Bearth. The magnetic field provided by the coil of the uniform magnetic field coil module is increased depending on the increase of the current. That is, the increase of the magnetic field by each increase of 0.08 A will approximately increase the resonance frequency by 1,000 Hz. Thus, it will reduce difficulty of experiments for the user through rapidly adjusting the parameter to a correct Pulse frequency.

Figure 11:
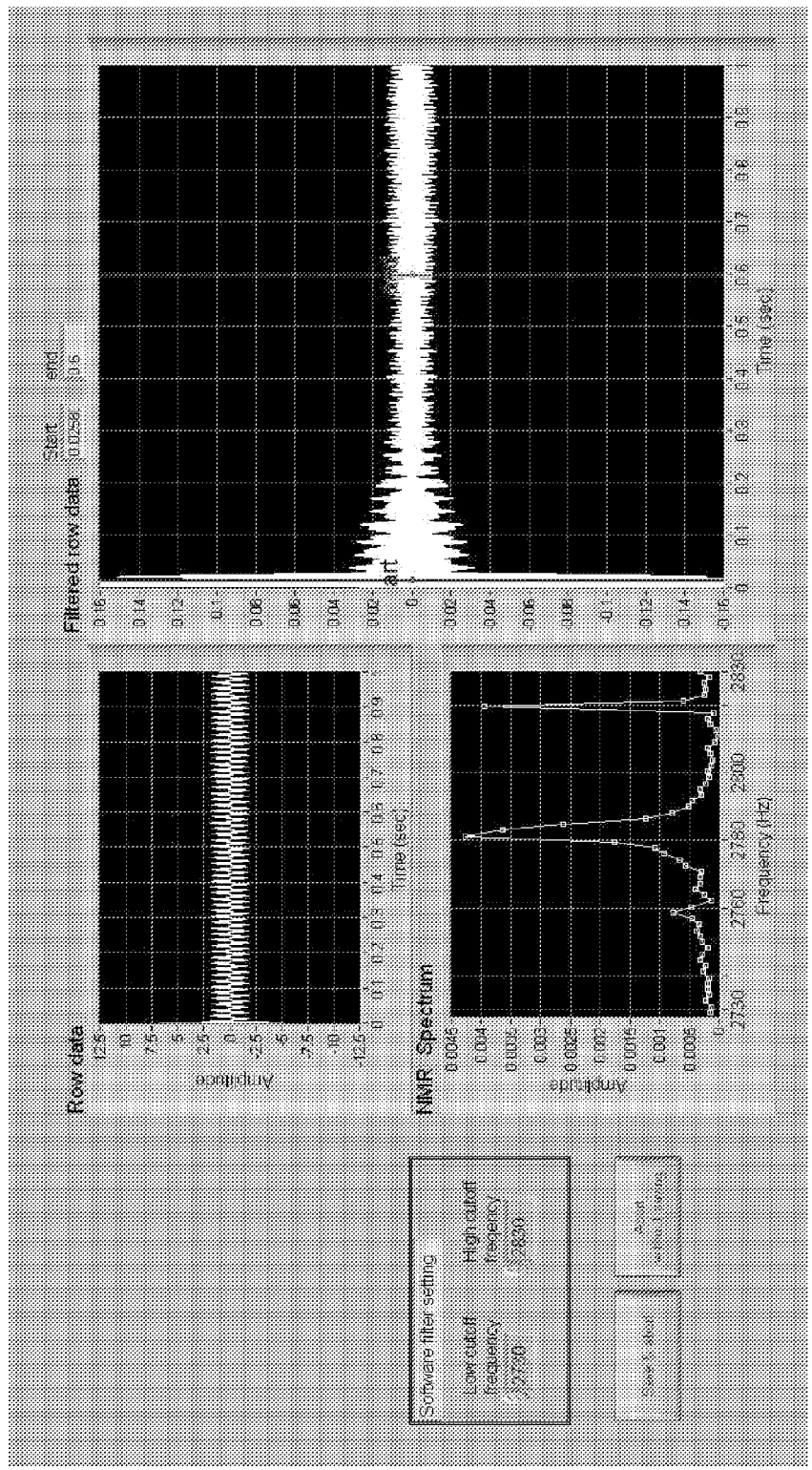
FIG. 11 shows window 2 for NMR measurement of the operational software of the NMR system according to the preferred embodiment of the invention.

During experimenting, it is first to input the value of current provided by the power source to the program to obtain a coil magnetic field at this time. After setting the Pulse frequency, it is then to move the sample and click "Start measurement" for the experiment (such a part is functionally the same as "NMR measurement" and will not be redundantly repeated here). The obtained NMR spectrum is shown in the left-lower part of the drawing. At this time, it may move a yellow line in the drawing to a resonance frequency and then to record the resonance frequency, as shown in FIG. 11.

After pressing either "Record and save" or "Record without save", it will record the value of the Resonance frequency in the left-lower part of the drawing and record in the right part the value of Bcoil, shown in the right part of "Frequency v.s. Bcoil" in the drawing, in which Bcoil is calculated by the previously set Icoil. The difference between the two lies in if there exists "Row data". If the experiment in this time fails, it may press down "Abort". As such, it will not record the resonance frequency and Bcoil. When pressing any one of the three buttons, the screen will return to the previous state of no measurement. At this time, if changing Icoil and Pulse frequency and repeatedly measuring NMR to record the resonance frequency, the program will automatically proceed with fitting Frequency v.s. Bcoil and calculate the gyromagnetic ratio and Bearth. After the experiment, it will return to the main window of FIG. 9 after pressing "Return".

2. $T_2^*$ Fitting

Figure 12:
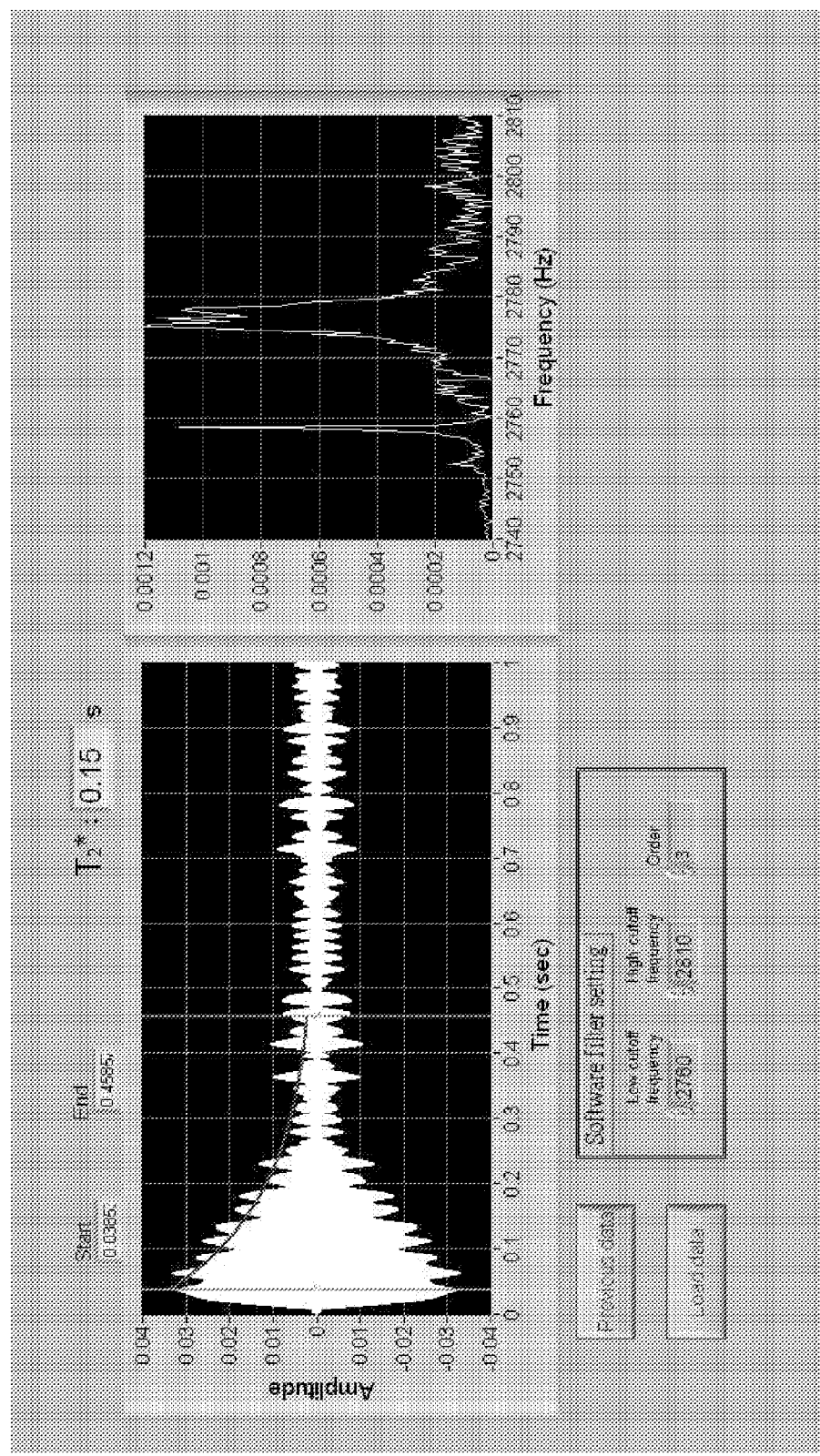
FIG. 12 shows window for $T_2^*$ fitting measurement of the operational software of the NMR system according to the preferred embodiment of the invention.

After clicking "$T_2^*$ fitting", a new window will appear, as shown in FIG. 12.

At this time, if the user has just finished NMR measurement, he may click on Previous data to automatically read in the row data proceeded in the previous NMR measurement or press down Load data to read in the data stored on the file in the previous experiment for proceeding with analysis. The data after reading in and being filtered by the software will show in the left drawing. The right drawing shows the spectrum obtained through Fourier Transformation for the data in the left drawing. The user may set Software filter setting to reduce noise so as to render the value of the fitting more accurate. The area selected by the blue line in the left drawing will automatically proceed with fitting, and the function selectively used for use is a $\exp(-t/T_2^*)$, which is a functional format of NMR FID. The curve of the fitting will shown in the left drawing by a red line and the $T_2^*$ obtained by the fitting is also shown in the drawing. After analysis, the user may click on "Return" to come back to the main window in FIG. 9.

Figure 13:
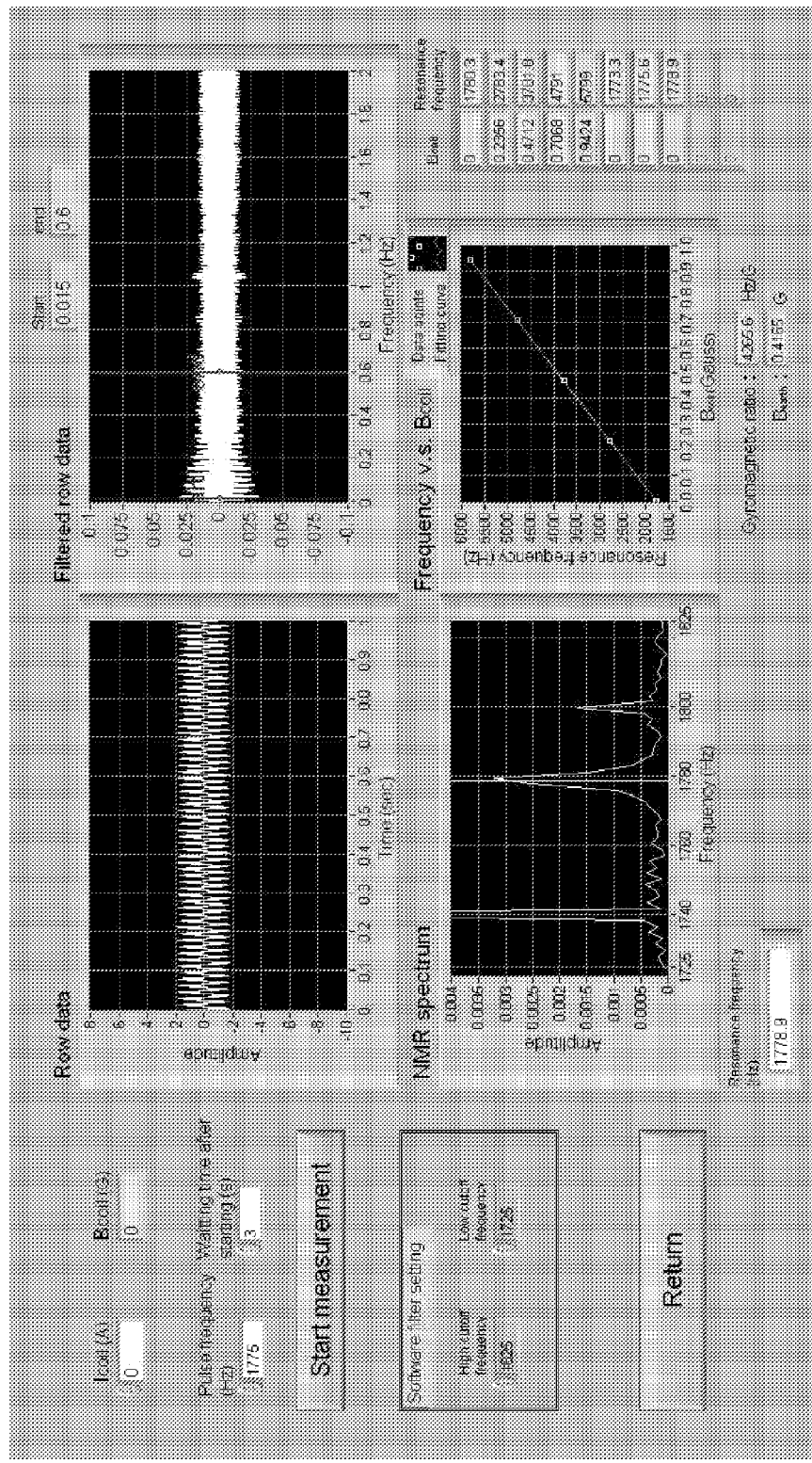
FIG. 13 shows window 1 for gyromagnetic ratio measurement of the operational software of the NMR system according to the preferred embodiment of the invention.

3. Gyromagnetic Ratio Measurement:

After clicking on the "Gyromagnetic ratio measurement" on the main window, it will appear such a window as shown in FIG. 13.

The experimental operation part thereof is the same as that of the NMR measurement. It is mainly provide the user to alter Icoil and Pulse frequency for proceeding with the magnetic resonance experiment in different magnetic fields and recording the resonance frequency to calculate the Gyromagnetic ratio and Bearth. In the embodiment, the magnetic field provided by the coil will be increased in dependence of the increase of the current. The increase of the magnetic field by each increase of 0.08 A will approximately increase the resonance frequency by 1,000 Hz. Thus, it will reduce difficulty of experimenting for the user through rapidly adjusting the parameter to a correct Pulse frequency.

Figure 14:
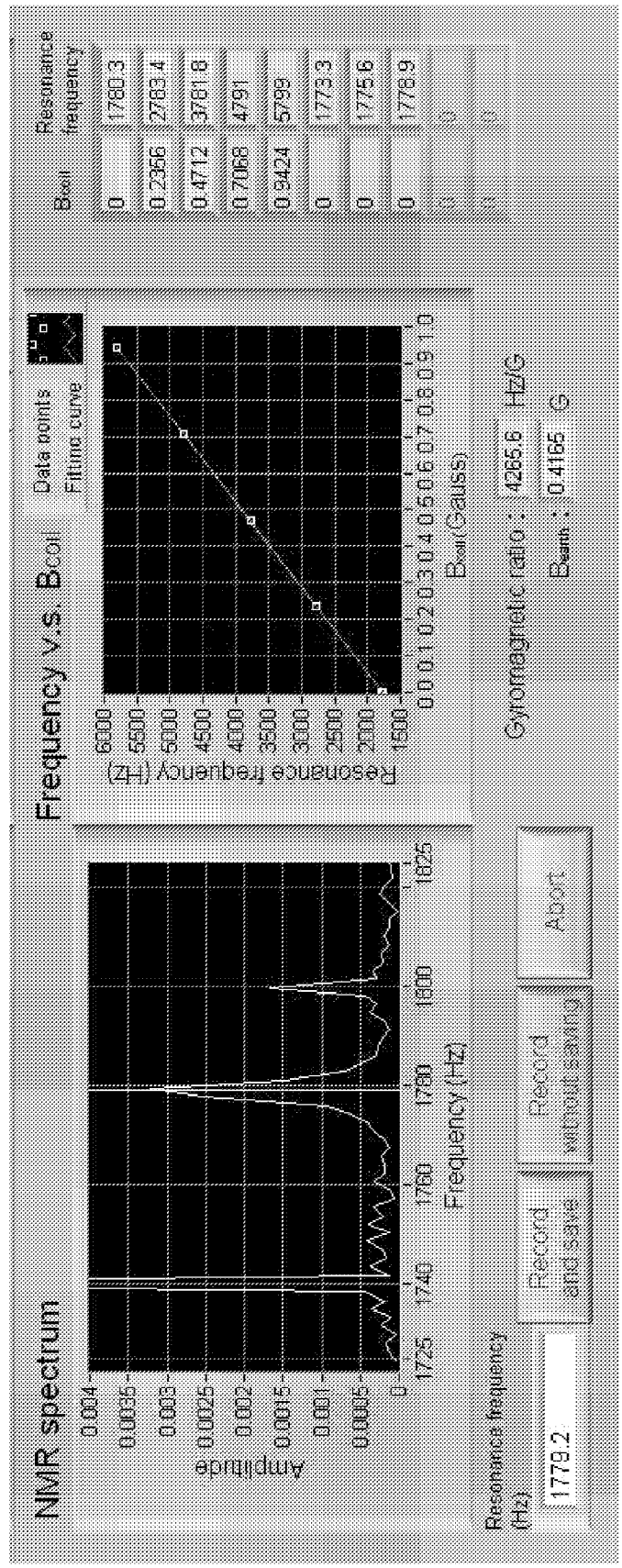
FIG. 14 shows window 2 for gyromagnetic ratio measurement of the operational software of the NMR system according to the preferred embodiment of the invention.

During experimenting, it is first to input the current provided by the power source to the program to obtain the magnetic field of the coil at that time. After setting the Pulse frequency, it is then to move the sample and click on "Start measurement" for proceeding with the experiment (such a part is functionally the same as "NMR measurement" and will not be redundantly repeated here). The obtained NMR spectrum is shown in the left-lower part of the drawing. At this time, it may move a yellow line in the drawing to a resonance frequency and then to record the resonance frequency, as shown in FIG. 14.

After pressing either "Record and save" or "Record without save", it will record the value of the Resonance frequency in the left-lower part of the drawing and record in the right part the value of Bcoil, shown in the right part of "Frequency v.s. Bcoil" in the drawing, in which Bcoil is calculated by the previously set Icoil. The difference between the two lies in if there exists "Row data". If the experiment in this time fails, it may press down "Abort". As such, it will not record the resonance frequency and Bcoil. When pressing any one of the three buttons, the screen will return to the previous state of no measurement. At this time, if changing Icoil and Pulse frequency and repeatedly measuring NMR to record the resonance frequency, the program will automatically proceed with fitting Frequency v.s. Bcoil and calculate the gyromagnetic ratio and Bearth. After experimenting, it will return to the main window of FIG. 9 after pressing "Return".

Application of J-Coupling Detection:

J-coupling refers to split of a signal caused by interaction of self-spin of an adjacent nucleus, which has no concern with the magnitude of an externally applied magnetic field. As a minor magnetic field produced by the self-spin of a nucleus affects an adjacent nucleus to thereby incur a J-coupling signal, the signal distance produced by its splitting will be affected by the number of the chemical bond between nucleuses. The number of the chemical bond determines the frequency difference between split peaks and the difference value is called coupling constant, while the nucleuses interacted each other will have the same coupling constant. The geometrical construction of a molecule may be obtained from the coupling constant, such as the angle between atoms and the folding relation between molecules. As the bondage number between the atoms is getting bigger, the effect between the nucleuses is becoming smaller, such that the coupling constant is becoming smaller. However, the number of the nucleuses having $I=\frac{1}{2}$ will determine the amplitude magnitude and the number of the peaks of a split signal. This application is to measure the structural formula and Hamiltonian of $(CH_3)_3PO_4$ as follows:

(a)

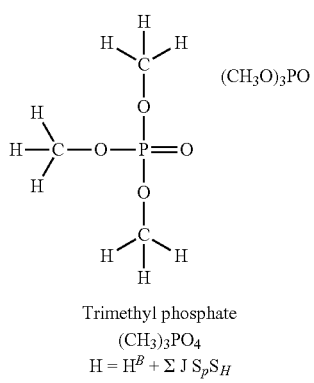

(CH₃O)₃PO

Trimethyl phosphate
$(CH_3)_3PO_4$
$H = H^B + \Sigma J S_p S_H$

Figure 7:
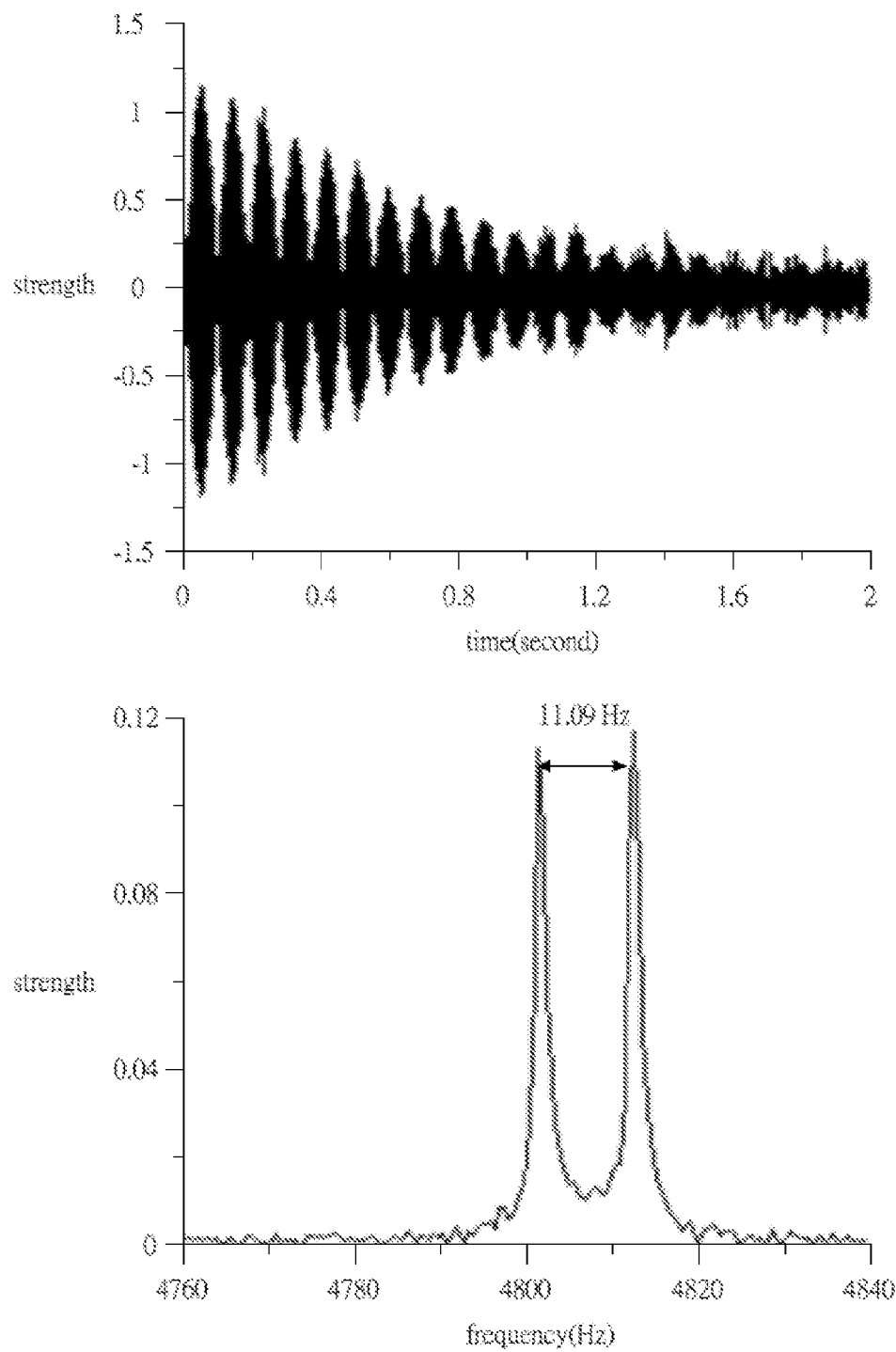
FIG. 7 shows NMR data and Fourier Transformation spectrum for J-coupling detection according to the preferred embodiment of the invention.

Since there is interaction between $^{31}P$ and $^1H$, there is an additional $\Sigma JS_p S_H$. Due to that H is effected on by one P, its energy state is divided into two energy states because nuclear spin of the two elements is in the same direction or reverse direction. Therefore, the NMR spectrum is split into two peaks. FIG. 7 shows NMR row data measured at 1.13 Gauss and a spectrum after Fourier Transformation.

Although the present invention has been explained in relation to its preferred embodiments, it is to be understood that other possible modifications and variations can be made by those skilled in the art without departing from the scope of the invention as claimed below.

The invention claimed is:

1. A low-field nuclear magnetic resonance system for measuring a magnetic resonance signal of an object to be measured, comprising:
   a pre-magnetization module including at least two magnets having the same size, the pre-magnetization module forming a receiving space between the two magnets to receive the object to be measured and establishing a pre-magnetization field for the object to be measured;
   a uniform magnetic field coil module including a tilt angle adjusting unit and a magnetic field coil unit, in which the tilt angle adjusting unit comprises a tilt bottom base, being adjustable in its tile angle, and the magnetic field coil unit is placed on an inclined plane of the tilt bottom base and comprises a coil set and a power source, wherein the coil set includes two pairs of coils with different radius, being allocated in a concentric circle manner and being electrically connected to the power source, thereby adjusting background magnetic field intensity of the magnetic resonance;
   a pulse and receiving coil module including a pulse coil, a receiving coil and a preamplifier, in which the pulse coil provides a pulse magnetic field for changing a direction of an atomic nuclear magnetic torque of the object to be measured, the receiving coil detects a precession magnetic signal of the magnetic torque and outputs an electric signal to be fed to the preamplifier, and the preamplifier outputs a first amplified signal;
   a filter amplifier module including a filter amplifier circuit, for receiving the first amplified signal, filtering noise and outputting a second amplified signal;
   a signal acquisition module being respectively electrically connected with the pulse coil and the filter amplifier module for receiving the second amplified signal and outputting an acquisition signal; and
   a processing module electrically connected to the signal acquisition module, for receiving and analyzing to process the acquisition signal.

2. A low-field nuclear magnetic resonance system as claimed in claim 1, wherein the magnets are of Nd—Fe—B magnet.

3. A low-field nuclear magnetic resonance system as claimed in claim 1, wherein the magnitude of the angle adjustable for the tilt angle is 0-50 degrees.

4. A low-field nuclear magnetic resonance system as claimed in claim 1, wherein the power source is a DC source.

5. A low-field nuclear magnetic resonance system as claimed in claim 1, wherein the pulse and receiving coil module is placed in an Aluminum shielding box.

6. A low-field nuclear magnetic resonance system as claimed in claim 5, wherein the receiving coil and the preamplifier of the pulse and receiving coil module are respectively placed in an Aluminum shielding box further.

7. A low-field nuclear magnetic resonance system as claimed in claim 1, wherein the processing module further includes a programming object for controlling timing processing and signal analysis in measurement process.

8. A low-field nuclear magnetic resonance system as claimed in claim 7, wherein the programming object provides a function of nuclear magnetic resonance measurement, $T_2^*$ fitting measurement, or gyromagnetic ratio analysis, or a combination thereof.

9. A low-field nuclear magnetic resonance system as claimed in claim 8, being used in an object to be measured for measuring a nuclear magnetic resonance result, spin-spin relaxation parameter or gyromagnetic ratio data or a combination thereof.

10. A low-field nuclear magnetic resonance system as claimed in claim 8, being used in an object to be measured for measuring a J-coupling detection.

* * * * *